United States Patent
Hawkes et al.

(10) Patent No.: US 8,268,013 B2
(45) Date of Patent: Sep. 18, 2012

(54) HAIR TREATMENT COMPOSITION AND METHODS

(75) Inventors: Jamie Anthony Hawkes, Leeds (GB); David Malcolm Lewis, Otley (GB); Celine Gauche, Leeds (GB)

(73) Assignee: Perachem Limited, Leeds Yorkshire (GB)

( * ) Notice: Subject to any disclaimer, the term of this patent is extended or adjusted under 35 U.S.C. 154(b) by 0 days.

(21) Appl. No.: 13/171,836

(22) Filed: Jun. 29, 2011

(65) Prior Publication Data

US 2011/0256081 A1 Oct. 20, 2011

Related U.S. Application Data

(63) Continuation of application No. 12/921,592, filed on Oct. 18, 2010, now Pat. No. 8,016,895.

(51) Int. Cl.
*D06L 3/10* (2006.01)
*A61Q 5/08* (2006.01)

(52) U.S. Cl. .................. 8/101; 8/109; 424/62

(58) Field of Classification Search .............. 8/101, 109; 424/62
See application file for complete search history.

(56) References Cited

U.S. PATENT DOCUMENTS

| | | | |
|---|---|---|---|
| 2,236,970 A * | 4/1941 | Goldfarb | 424/62 |
| 6,398,822 B1 | 6/2002 | Brock et al. | |
| 6,713,613 B1 | 3/2004 | Lewis et al. | |
| 6,716,969 B1 | 4/2004 | Lewis et al. | |

FOREIGN PATENT DOCUMENTS

| | | |
|---|---|---|
| WO | 9951195 A1 | 10/1999 |
| WO | 9951689 A1 | 10/1999 |
| WO | 2007039527 A2 | 4/2007 |

OTHER PUBLICATIONS

Patent cooperation Treaty (PCT) International Search Report for PCT/GB2009/050233 dated Jul. 22, 2010, 6 pages.
Patent cooperation Treaty (PCT) Written Opinion of the International Searching Authority for PCT/GB2009/050233 dated Sep. 14, 2010, 9 pages.
Elhilo, Notice of Allowance and Fee(s) Due for U.S. Appl. No. 12/921,592, filed Jun. 14, 2011, 4 pages.
Elhilo, Corrected Notice of Allowance and Fee(s) Due for U.S. Appl. No. 12/921,592, filed Jul. 1, 2011, 10 pages.
Shrestha, STIC Search Report dated Mar. 29, 2011, 117 pages.
Conair Corp., Material Safey Data Sheet for "Rusk ID ELIMIN 8 Color Corrector Color Reducer 1," Jul. 1999, 2 pages.
Conair Corp., Material Safey Data Sheet for "Rusk ID ELIMIN 8 Color Corrector Conditioning Catalyst 2," Jul. 1999, 2 pages.
Conair Corp., "Rusk ELIMIN 8 Color Corrector," Product Sheet, Date Unknown, 1 sheets.
Conair Corp., "Rusk ELIMIN 8 Color Corrector," Product Box, Date Unknown, 1 sheets.

* cited by examiner

*Primary Examiner* — Eisa Elhilo
(74) *Attorney, Agent, or Firm* — Stephen F. Swinton, Jr.; Hoffman Warnick LLC

(57) ABSTRACT

In one embodiment, the invention provides a method of removing color from dyed hair, the method comprising applying to the hair a color removal composition comprising a sulfur-containing nucleophile or a precursor thereof.

5 Claims, No Drawings

HAIR TREATMENT COMPOSITION AND METHODS

CROSS-REFERENCE TO RELATED APPLICATIONS

This application is a continuation of U.S. patent application Ser. No. 12/921,592, now U.S. Pat. No. 8,016,895, having an effective U.S. filing date of 18 Oct. 2010, which is hereby incorporated herein.

The present invention relates to compounds suitable for colouring materials, in particular keratinous fibre materials, for example hair; to compositions comprising the same, and to methods and uses relating thereto.

In a preferred embodiment the invention relates to a process of colouring keratinous fibre materials, for example hair, and then optionally removing colour from the material, whilst limiting damage to the material. The colouring and colour removal stages can be carried out in quick succession or with a reasonable time period in-between them. The colouring and colour removal stages can be repeated many times, with limited damage to the material, for example hair.

The desire to alter the colour of human hair is not a facet of modern times. Since the days of the Roman Empire the colour of human hair has been routinely altered to accommodate the changes of fashion and style. However the attainment of precise initial colours which are retained by the hair for a desirable period has remained a more elusive goal. The difficulties in the development of hair colouring compositions which can deliver precise long-lasting colours are in part due to the inherent structure of the hair itself and in part due to the necessary conditions of effective hair colouration processes.

In general, the condition and structure of human hair is not regular along the length of the hair shaft. Human hair is subject to various chemical and mechanical treatments, for example combing, brushing, shampooing, heating, perming and straightening as well as exposure to the sun. As such, the hair at the ends of the hair shaft will generally exhibit greater signs of damage relative to the new growth close to the scalp. This damage can lead to inconsistent colouration when the hair is dyed due to irregular uptake of the hair colouring agents along the length of the hair shaft.

Once the hair has been coloured there is a desire for the colour to be resistant to fading, as occasioned by the actions of washing (also known as wash fastness), perspiration, hair spray and other exterior factors such as the action of the sun, and further that the colour be retained in a consistent manner for a predictable period of time. Additionally damage to the hair that can lead to irregular dye uptake as discussed above, can lead to increased fading of the damaged portions of the hair and consequently, irregular levels of colour fade over time. An additional difficulty commonly associated with the dyeing of human hair is the need for dye systems which avoid any adverse effect on the hair and skin of the user, such as brittle hair, or, irritation of the skin, or, staining (colouring) of the skin.

Thus, it would be desirable to develop a hair colouring composition which exhibits reduced fade, provides improved resistance to wash out during a regular cleansing regime, can deliver substantially consistent hair colour results throughout the hair, which has reduced irritant effect on the skin, which has reduced staining on the skin, which has reduced adverse effects on the hair of the user and also to develop a convenient and easy-to-use method for the delivery of such a hair colouring composition to the hair.

Although it is desirable to provide hair colouring compositions which are resistant to fade, on occasions a user may wish to remove colour from dyed hair. Currently if this is desired, it is necessary to treat the dyed hair with oxidising bleaches. However, repeated colouring and oxidative bleaching of the dyed hair can lead to significantly damaged hair. It would thus be highly desirable to provide a hair colouring composition which could easily be removed from the hair without oxidatively bleaching the dyed hair and thus limiting any damage to the hair.

Over the years significant effort has been directed towards the elimination of many of the problems associated with the dyeing of human hair. Various approaches to hair dyeing have been developed including the use of oxidative dyes, direct action dyes, natural dyes, metallic dyes and reactive dyes.

Reactive dye hair colouring agents can be used to deliver a variety of hair colours to the hair. However substantial improvement is needed in the areas of colour saturation colour development, precise initial colour consistency, improved wash fastness, improved hair condition and reduced levels of hair damage. It is also necessary to consider the environmental impact of chemicals used as hair colouring agents.

Thus there is a need for reactive dye hair colouring compounds and compositions which show improved properties compared with those of the prior art. Facility to dye other keratinous fibres, for example wool, cashmere, mohair and alpaca, would be an advantage.

According to a first aspect of the present invention there is provided compounds of formula (I)

$$D\text{-}L\text{-}CHQ\text{-}CH_2\text{—}SR \qquad (I)$$

wherein D is a chromophore; L is a linking group selected from $SO_2$, NHCO, and $NHSO_2$; Q is a hydrogen or halogen atom; and R is selected from $C_1$-$C_4$ alkyl, $(CH_2)_n COOH$, $(CH_2)_n CONH_2$, $(CH_2)_n SO_3 H$, $(CH_2)_n COOM$, $(CH_2)_n PO_3 H$, $(CH_2)_n OH$, $(CH_2)_n SSO_3^-$, $(CH_2)_n NR^1{}_2$, $(CH_2)_n N^+ R^1 H_2$, $(CH_2)_n NHCOR^1$, $PhSSO_3^-$, $PhSO_3 H$, $PhPO_3 H$, $PhNR^1{}_2$, $PhN^+ R^1{}_3$, $(CH_2)_2 CH(SH)R^1 (CH_2)_3 COOH$, and

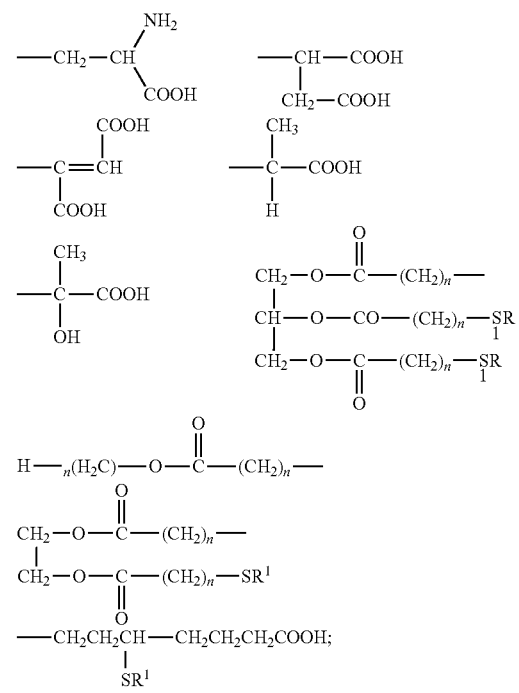

n is an integer in the range of 1 to 4 wherein within the same molecule each n is not necessarily the same integer; M is a cation of an alkaline earth metal, alkali metal, $NH_4^+$ or $NR^1_3{}^+$; and $R^1$ is $C_1$-$C_4$ alkyl.

When there is more than one group $R^1$ within a molecule each may be the same or different.

One preferred sub-class of compounds of formula (I) may be defined as

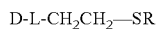        (IA)

where D, L and R are as defined above.

Another preferred sub-class of compounds of formula (I) may be defined as

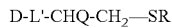        (IB)

where D, Q and R are as defined above and L' represents a linking group NHCO. In this sub-class Q is preferably a halogen atom.

Esters and salts of the acidic residue compounds falling within the above definition are also within the scope of the present invention.

Linking group L is preferably selected from $SO_2$ and NHCO. $SO_2$ is especially preferred.

A halogen atom (Hal) is suitably a fluorine, chlorine, bromine or iodine atom; preferably a chlorine or, especially, a bromine atom.

The use of such compounds as colouring agents for keratinous fibre materials, notably hair, have shown a number of benefits, for example improved wash fastness of dye on fibres, less colour fade over time, improved consumer acceptance, improved colour consistency and saturation, improved fibre condition, reduction in fibre damage and skin irritation, and an improved health and safety and/or environmental profile.

The novel compounds of the present invention comprise a thioether bonded to an ethylene group which at the other terminus is bonded to a linking group, for example the carbon atom of an amide or a sulfur atom of sulfone. The linking group is in turn bonded to a chromophore moiety, preferably to a carbon atom thereof.

The group SR in formula I is preferably $SCHR^2R^3$.

In preferred embodiments compounds of the present invention have a structure shown in formula (II) or (IIA).

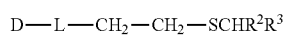        (II)

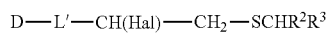        (IIA)

where D, L, L' and Hal are as defined above.

Preferably $R^2$ is selected from $(CH_2)_mCOOX$, $(CH_2)_mSO_3X$, $(CH_2)_mNH_2$, $(CH_2)_mNR^4R^5$, $(CH_2)_mNHCOR^4$ and $(CH_2)_mCH(COOX)NH_2$; wherein m is an integer of from 0 to 3, and X is selected from hydrogen, an alkali metal, a $C_1$ to $C_4$ alkyl group and a substituted or unsubstituted ammonium salt; $R^4$ is a $C_1$ to $C_4$ alkyl group and $R^5$ is selected from hydrogen and a $C_1$ to $C_4$ alkyl group.

Preferably m is 0 or 1. X is preferably selected from hydrogen, sodium, potassium, $NH_4$ or $NH(R^6)_3$ wherein each $R^6$ is a $C_1$ to $C_4$ alkyl, for example methyl.

$R^3$ is preferably selected from hydrogen, an alkyl group having 1 to 4 carbon atoms, an ester, an acid, an amide, an amine residue or an alcohol residue.

Especially preferred compounds of the present invention are those of formulae (III) and (IV):

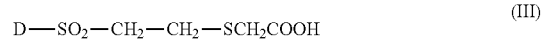        (III)

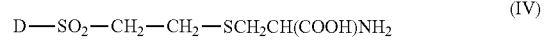        (IV)

and esters and salts thereof. Suitable esters include methyl and ethyl esters. Suitable salts include alkali metal and ammonium salts.

The compounds of the present invention include a chromophore moiety D.

Any chromophore moieties suitable for use for dyeing substrates can be used in the present invention. The term chromophore as used herein means any photoactive compound and includes any coloured or non-coloured light absorbing species, e.g. fluorescent brighteners, UV absorbers, IR absorbing dyes.

Suitable chromophore moieties for use in the dye compounds herein include the radicals of monoazo, bisazo or polyazo dyes or of heavy metal complex azo dye derived therefrom or of an anthraquinone, phthalocyanine, formazan, azomethine, dioxazine, phenazine, stilbene, triphenylmethane, xanthene, thioxanthene, nitroaryl, naphthoquinone, pyrenequinone or perylenetetracarbimide dye. Most preferred for dyeing hair in the short times and low temperatures favoured by the present invention are those chromophores which have a molecular mass of less than 1500.

Suitable chromophore moieties for use in the dye compounds herein include those disclosed in EP-A-0,735,107 (Ciba-Geigy), incorporated herein by reference, including the radicals described therein which contain substituents customary for organic dyes, such as sulfonate substituents which enhance the water-soluble properties of the dye compound.

Preferred chromophore moieties D are those based on azo compounds, anthraquinone dyes or phthalocyanine dyes.

Preferred azo chromophore moieties for use in the present invention include monoazo species of formula (V) and bisazo species of formula (VI).

        (V)

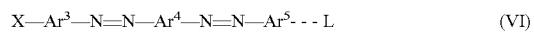        (VI)

It is indicated by the dashed lines in the structures which part of each molecule is bonded to linking group L.

Each of $Ar^1$, $Ar^2$, $Ar^3$, $Ar^4$ and $Ar^5$ independently represent an optionally-substituted aromatic residue. These may be based on one or more aromatic ring structures preferably selected from benzene, naphthalene, anthracene, phenanthrene, piperidine, imidazole, parazole, pyrazalone, oxazole, thiophene, benzopyrene, quinoline, isoquinoline, chromine, isochromine, indole, isoindole, benzofuran, benzamidazole and pyrazole.

In some embodiments as detailed above the aromatic residue may comprise a fused ring system. Alternatively each or any of $Ar^1$, $Ar^2$, $Ar^3$, $Ar^4$ and $Ar^5$ may comprise two or more aromatic rings linked together via a single covalent bond.

In preferred embodiments each of $Ar^1$, $Ar^2$, $Ar^3$, $Ar^4$ and $Ar^5$ is independently selected from structures based on benzene, naphthene, pyrazole and adducts thereof.

Any of said aromatic moieties $Ar^1$, $Ar^2$, $Ar^3$, $Ar^4$ and $Ar^5$ may be substituted with one or more substituents selected from hydroxy, nitro, amino, amido, COOH, halo, ether, thioether, sulfoxyl, cyano, thiocyano, ester and alkyl, for example methyl.

Preferably at least one of Ar¹ and Ar² in structure (V) is substituted with a group SO₃Y, wherein Y is hydrogen or an alkali metal or ammonium salt. Preferably Y is sodium. Each of Ar¹ and Ar² may include such sulfonate residues. Either or both of Ar¹ and Ar² may be polysulfonated, that is either or each may include more than one SO₃Y residues.

In structure (VI), each or any of Ar³, Ar⁴ and Ar⁵ may be optionally substituted with one or more residues selected from amino, hydroxy, amido, COOH, ester, thioether, sulfoxy, cyano, thiocyano, ether, thioether, halo and alkyl for example methyl. Preferably at least one of Ar³, Ar⁴ and Ar⁵ is sulfonated.

In structure (VI) X may be selected from hydrogen, hydroxide, nitro, amino, ester, COOH, ether, amido, halo, alkyl, alkoxy, sulfoxy and thioether. Preferably X is a second group of the formula LCH₂CH₂SR.

Preferred anthraquinone chromophore moieties are those of formula (VII)

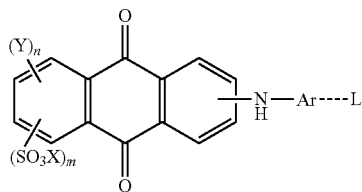

(VII)

wherein n is from 0 to 6, m is from 0 to 6, X is selected from hydrogen and alkali metal and Y is selected from hydroxy, amino, amido, COOH, ether, ester, thioether or sulfoxy, alkyl, halo or nitro. The substituents Y and SO₃X may be present on either or each of the benzene rings. In preferred embodiments n is 1 or 2, m is 1 or 2, X is sodium and Y is NHCOCH₃, CH₃ or OH. Ar represents an aromatic residue, preferably a benzene residue which, as indicated by the dashed bond, is substituted with the group L-CH₂CH₂SR.

Anthraquinone dyes are useful for providing light fast blue chromophore moieties. Especially preferred compounds are those having 1,4-diamino or 1,4-substituted diamino derivatives. The sulfo group is preferably at the 2-position.

Preferred phthalocyanine dyes are those based on copper phthalocyanine, especially sulfonated or polysulfonated residues thereof. These compounds provide chromophores of brilliant turquoise blues and emerald greens. An example of such a compound is shown in formula (VIII).

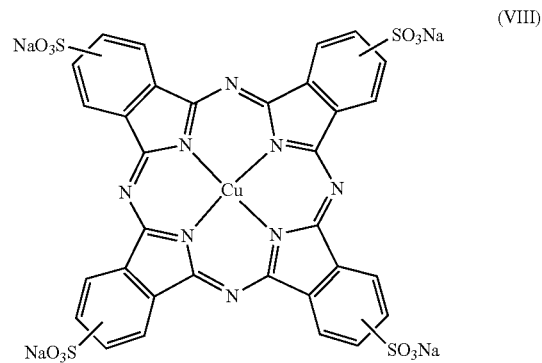

(VIII)

Other such copper phthalocyanine compounds may be monosulfonated, disulfonated or trisulfonated. The above compounds are converted to the sulfonyl chloride and then reacted with m-base (1-aminobenzene-3-sulfatoethylsulfone) or p-base (1-aminobenzene-4-sulfatoethylsulfone) under mild alkaline aqueous conditions to provide a mixture including sulfatoethylsulfone compounds. Subsequent reaction with an appropriate thiol provides compounds of the present invention having the formula (RSCH₂CH₂SO₂—Ar—NHSO₂)₁₋₃CuPc-(SO₃H)₁₋₃ where CuPc is a copper phthalocyanine residue.

Especially preferred chromophore groups D for use herein are those present in Remazol® dyes commercially available from Dystar. Compounds of this type, incorporating such chromophore moieties, are believed to be denoted by representative formulae IXa, IXb, IXc, IXd and IXe.

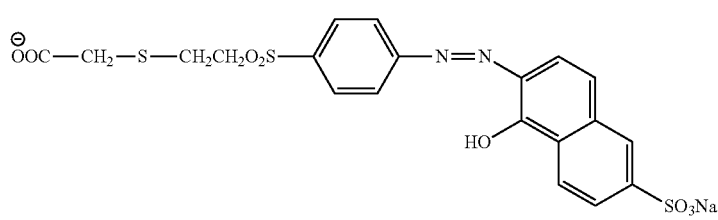

IXa

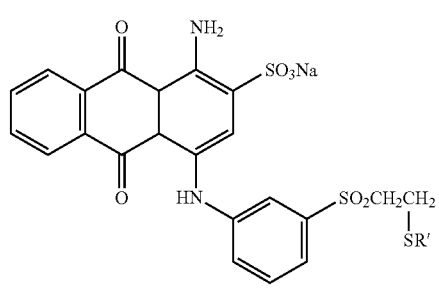

IXb

-continued

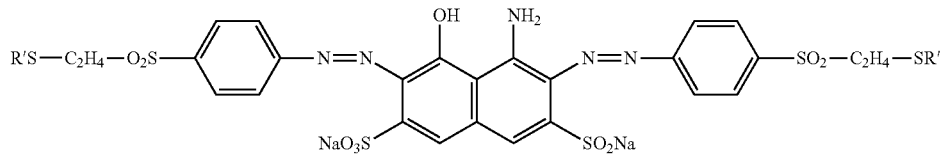

IXc

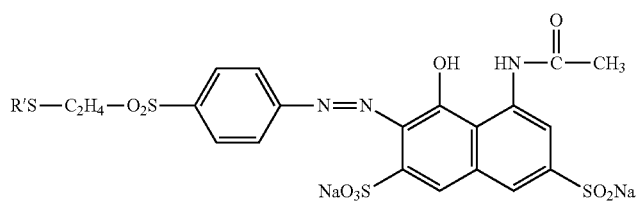

IXd

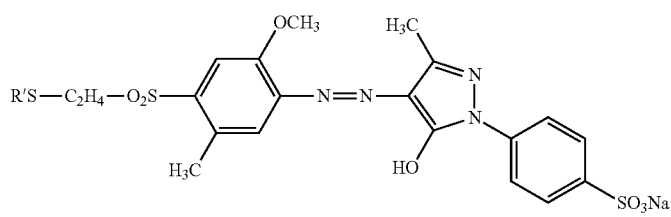

IXe

The compounds of formula IXa is orange, that of IXb is blue, that of IXc is black, that of IXd is red and that of IXe is yellow. It will be appreciated that the formation of mixtures of two or more of these compounds in differing amounts enables a wide variety of colours to be obtained.

According to a second aspect of the present invention there is provided a method of preparing compounds of the first aspect, the method comprising reacting a compound of formula (X) or (X') with a thiol of formula (XI):

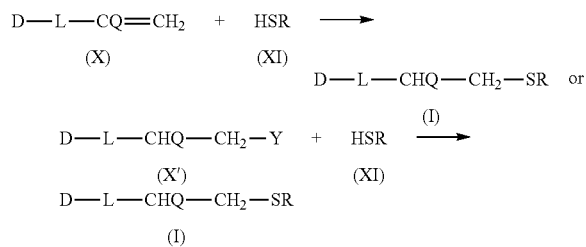

wherein R, D and L are as defined in relation to the first aspect and Y is a leaving group.

Y is preferably selected from a halogen, especially chlorine, $OPO_3H$, $OSO_3H$, $SSO_3H$ and $NR^1R^2R^3$, where $R^1$ and $R^2$ are $C_{1-4}$ alkyl and $R^3$ is hydrogen or $C_{1-4}$ alkyl.

The compounds of formula X or X' may be regarded as dye precursor materials.

In the method of the second aspect the compounds of formula X or X' are suitably reacted with the thiol XI under standard reaction conditions. Such conditions will readily be understood by those skilled in the art.

Typically, these reactions are carried out at a temperature of from −10 to 70° C., preferably from 0 to 60° C., for example between 20 and 50° C.

Suitably the reaction is carried out at a pH of between 6 and 12, preferably from 7 to 11.

A preferred solvent for carrying out the reaction of the second aspect is water.

The reaction may be carried out in a mixed aqueous solvent system, for example an aqueous alcoholic solution or a mixture of water and DMF.

The method of the second aspect may be used to prepare a mixture of compounds of the first aspect. In such cases the method may comprise reacting two or more compounds of formula X and/or X' with one or more thiols of formula XI; or reacting one or more compounds of formula X and/or X' with two or more thiols of formula XI. The mixture of the products obtained will be related to the mixture of reactants and may be adjusted according to the colour and other desired properties of the product.

Compounds of formula X and X' are known classes of compounds and may be made by methods known in the art, or by analogous methods. The compounds in which L comprises the group $SO_2$ have been used or proposed as chromophore-containing precursors for many dye molecules (not having the terminal group —SR), as have the compounds containing the group NHCO. For example GB 1037648 and GB 1351976 may be cited as describing applicable methods. Useful background may also be found in the book "Wool Dyeing", Ed. D. M. Lewis, Society of Dyers and Colourists, Bradford, 1992, pp. 225-227.

According to a third aspect of the present invention there is provided a composition for colouring a material, comprising one or more compounds of the first aspect, an optional diluent (or carrier) and further optional ingredients.

Preferably the composition is a composition for colouring a keratinous material. More preferably it is a composition for colouring a keratinous fibre material, although it may also be used to dye non-fibrous keratin based material, for example fingernails.

A keratinous fibre material may be derived from an animal's coat or pelt (for example wool, or cashmere, or mohair, or angora or alpaca) but is preferably human hair. For convenience the word "hair" is used hereafter but it is to be understood that the invention is broader in its scope and that the following definitions apply to materials in general.

The composition may be provided as a concentrated composition which upon dilution can be applied to the hair to provide the desired colour. In some embodiments, the composition may consist essentially of a mixture of two or more compounds of the first aspect.

In preferred embodiments the composition of the third aspect comprises a ready-to-use formulation which can be directly applied to hair to effect the dyeing thereof.

The ready-to-use hair colouring formulations of the present invention preferably comprise at least 0.001 wt % of one or more compounds of the first aspect, preferably at least 0.005 wt %, more preferably at least 0.01 wt %, preferably at least 0.05 wt % and most preferably at least 0.1 wt %. Such formulations may comprise up to 25 wt % of one or more compounds of the first aspect, for example up to 20 wt % or 15 wt %, preferably up to 10 wt %, more preferably up to 7 wt %, preferably up to 5 wt % and most preferably up to 3 wt %.

The types and levels of dyes used in each composition will depend upon the desired hair shade.

In addition to compounds of the first aspect, the composition of the third aspect may include one or more further ingredients. Such ingredients include a second thiol component, a pH control agent, a thickener, one or more surfactants, other dye materials and further additives as described herein. A diluent may suitably be included. The diluent may be present in compositions provided in concentrated form. A diluent is present in embodiments in which the composition is provided as a ready-to-use formulation.

The composition of the third aspect of the present invention is preferably provided as a stable composition. Such a composition may suitably be stored without significant decomposition thereof under ambient conditions in a sealed container for a period of at least a week, preferably at least a month, more preferably at least six months.

Preferably the compositions of the third aspect comprise a second thiol component. This is present in addition to the necessary amount of thiol of formula XI (typically one molar equivalent) which is reacted with the dye precursor of formula X or X'. In some embodiments the second thiol component may be the same as the thiol of formula XI. Thus in preferred embodiments a molar excess of total thiol (including the thiol of formula XI and the second thiol component) is provided. The molar ratio of total thiol (of formula XI and second thiol component) to dye precursor of formula X or X' is preferably at least 1.05:1, more preferably at least 1.1:1, for example at least 1.2:1, 1.5:1 or 2:1. It may be at least 5:1, or at least 10:1.

Suitably sufficient excess thiol is added such that when dyeing hair surface reduction of cystine disulfide to cysteine thiol is achieved. Without being bound by theory it is believed that cysteine thiol functions as the main reactive nucleophile that reacts with the dye compounds of the present invention. An additional benefit of using thiols is that they may open up the hair structure and allow penetration of other agents, including dyes.

As detailed above, the thiol of formula XI may comprise a mixture of thiols. The second thiol component may comprise a single thiol or a mixture of thiols which may include compounds which are the same or different to the thiols of formula XI.

Examples of suitable thiols for use as the second thiol component include thioglycolic acid, thiolactic acid, dihydrolipoate, thioglycerol, mercaptopropionic acid, cysteine, N-substituted cysteines, cysteamines, N-substituted cysteamines, thioethanol and 1-thiopropane 3-sulfonate. Thioglycolic acid is especially preferred.

Preferably the second thiol component is present in an amount of from 0.5 to 20% wt of the composition, preferably 1 to 15% wt, more preferably 1.5 to 10% wt. In the case when a second thiol component is the same compound as a thiol of formula (XI) these weight definitions refer to the amount of free thiol in the composition, i.e. thiol not consumed in the reaction between compounds (X) or (X'), and (XI).

Alternatively and/or additionally the hair colouring composition may further comprise a sulfite salt. This may in some embodiments replace some or all of the second thiol component. Preferred sulfite salts are alkali metal or ammonium salts. Most preferred is sodium sulfite.

The sulfite salt when present is preferably present in an amount of from 0.1 to 15 wt %, preferably from 0.5 to 10 wt %, more preferably from 1 to 5 wt %.

Another preferred ingredient herein is a substance which disrupts hydrogen bonding in the composition (a hydrogen bond breaker). Any hydrogen bond breaker suitable for use in a hair dye composition can be used herein. Suitable examples include lithium bromide, urea, resorcinol, catechol, dihydroxyacetone, formamide, potassium chloride and magnesium chloride. Particularly preferred for use herein is urea.

The colouring compositions of the present invention preferably have a pH in the range of from about 6 to about 11, preferably from about 7 to about 10.5, preferably about 9 to about 10.5. In order to maintain such a pH the compositions may contain one or more optional pH control agents.

Examples of alkaline pH control agents suitable for use in the present invention include ammonium hydroxide, ethylamine, dipropylamine, triethylamine and alkanediamines such as 1,3-diaminopropane, alkaline alkanolamines such as mono, di or tri-ethanolamine, preferably those which are completely substituted on the amine group such as dimethylaminoethanol, polyalkylene polyamines such as diethylenetriamine or a heterocyclic amine such as morpholine as well as the hydroxides of alkali metals, such as sodium and potassium hydroxide, hydroxides of alkali earth metals, such as magnesium and calcium hydroxide, basic amino acids such as alanine, leucine, iso-leucine, and histidine and alkanolamines such as dimethylaminoethanol, aminoalkylpropanediol and mixtures thereof. Preferred pH control agents include water soluble bases, for example carbonates and hydroxides of alkali metals and ammonium, and triethanolamine.

Especially preferred pH control agents for use herein include 2-amino-2-methyl-1-propanol, ammonium hydroxide, and sodium hydroxide.

The hair colouring compositions of the present invention may additionally include a thickener, suitably a cosmetically approved thickener, at a level of from about 0.05% to about 20%, preferably from about 0.1% to about 10%, more preferably from about 0.5% to about 5% by weight. Thickening agents suitable for use in the compositions herein include those specified for cosmetic use by the Scientific Committee on Consumer Products (SCCP) managed by the Directorate-General for Health and Consumer Protection of the European Commission. The SCCP approve a list of chemicals for use which is referred to as the INCI list (International Nomenclature of Cosmetic Ingredients list). Preferred thickening agents suitable for use in the compositions of the present invention include oleic acid, cetyl alcohol, oleyl alcohol, sodium chloride, cetearyl alcohol, stearyl alcohol, synthetic thickeners such as Carbopol, Aculyn and Acrosyl and mixtures thereof. Preferred thickeners for use herein are Aculyn 22®, steareth-20 methacrylate copolymer; Aculyn 44®, polyurethane resin and Acusol 830® acrylate copolymers which are available from Rohm and Haas, Philadelphia, Pa., USA. Additional thickening agents suitable for use herein include sodium alginate or gum arabic, or cellulose derivatives, such as methyl cellulose or the sodium salt of carboxymethylcellulose or some types of acrylic polymers.

The hair colouring compositions of the third aspect optionally contain urea. Without being bound by theory it is believed that urea helps to solubilise the dye compounds in the composition and/or denature keratinous proteins found in hair (and animal fibres) and increases the rate of reaction with the fibre substrate.

Urea may suitably be present in an amount of at least 2% wt of the composition, and preferably at least 5% wt.

Urea may suitably be present in an amount up to 30% wt of the composition, preferably up to 20% wt, most preferably up to 15% wt.

Suitable diluent materials for use in compositions of the present invention may be selected from the INCI list. Water is the preferred diluent for use in compositions of the present invention. However, such compositions may include one or more further solvents as additional diluent materials. Generally, solvents suitable for use in the colouring compositions of the present invention are selected to be miscible with water and innocuous to the skin. Solvents suitable for use as additional diluents herein include C1-C20 mono- or polyhydric alcohols and their ethers, glycerine, with monohydric and dihydric alcohols and their ethers preferred. In these compounds, alcoholic residues containing 2 to 10 carbon atoms are preferred. Thus, a preferred group of suitable diluents includes ethanol, isopropanol, n-propanol, butanol, propylene glycol, ethylene glycol monoethyl ether, and mixtures thereof. Water is the preferred principal diluent in the compositions of the present invention. Principal diluent, as defined herein, means, that the level of water present is higher than the total level of any other diluents.

The diluent is present at a level preferably of from about 5% to about 99.98%, preferably from about 15% to about 99.5%, more preferably from about 30% to about 99%, and especially from about 50% to about 98% by weight of the compositions herein.

In preferred embodiments, the diluent comprises at least 90 wt % water, more preferably at least 95 wt %. Suitably the diluent consists essentially of water.

The compositions of the present invention can additionally contain a surfactant system. Suitable surfactants for use in compositions of the present invention may be found on the INCI list. Suitable surfactants for inclusion in the compositions of the invention generally have a lipophilic chain length of from about 8 to about 22 carbon atoms and can be selected from anionic, cationic, nonionic, amphoteric, zwitterionic surfactants and mixtures thereof.

Suitable surfactant compounds for use in the present invention are of the conventional type known for use in hair dye formulations and will be well understood by those skilled in the art. Preferred surfactants are those favoured by the cosmetic industry, for example cocamidopropyl betaine which is gentle and non-allergenic.

The hair colouring compositions of the present invention may, in addition to the compounds of formula I, optionally include other dye materials (suitable options may be found on the INCI list). Optional other dyes suitable for use in the hair colouring compositions and processes according to the present invention include both semi-permanent, temporary and other dyes.

Non-oxidative dyes as defined herein include the so-called 'direct action dyes', metallic dyes, metal chelate dyes, fibre reactive dyes and other synthetic and natural dyes. Various types of non-oxidative dyes are detailed in: 'Chemical and Physical Behaviour of Human Hair' 3rd Ed. by Clarence Robbins (pp 250-259); 'The Chemistry and Manufacture of Cosmetics'. Volume IV. 2nd Ed. Maison G. De Navarre at chapter 45 by G. S. Kass (pp 841-920); 'cosmetics: Science and Technology' 2nd Ed., Vol. II Balsam Sagarin, Chapter 23 by F. E. Wall (pp 279-343); 'The Science of Hair Care' edited by C. Zviak, Chapter 7 (pp 235-261) and "Hair Dyes", J. C. Johnson, Noyes Data Corp., Park Ridge, U.S.A. (1973), (pp 3-91 and 113-139).

A number of additional optional materials can be added to the colouring compositions herein described each at a level of from about 0.001% to about 5%, preferably from about 0.01% to about 3%, more preferably from about 0.05% to about 2% by weight of composition. Such materials include proteins and polypeptides and derivatives thereof; water-soluble or solubilisable preservatives; moisturising agents; anti-bacterial agents; low temperature phase modifiers; viscosity control agents; quaternary amine compounds; hair conditioning agents; enzyme stabilisers; colouring agents; $TiO_2$ and $TiO_2$-coated mica; perfumes and perfume solubilisers; zeolites; $Ca^{2+}/Mg^{2+}$ sequestrants and water softening agents. A number of other formulation ingredients could be added to the composition, for example one or more of stabilisers, emulsion stabilisers, film formers, emulsifiers, antioxidants, chelators, antistatic agents, anti-caking agents, pH buffers, bulking agents, UV absorbers, moisturising agents, opacifiers, masking agents, reducing agents, humectants and foaming agents.

Examples of suitable compounds which may be used for such functions are well known to those skilled in the art and are preferably selected from those commonly used in hair dye formulations. A suitable reference point for lists of such materials can be found in the INCI list.

According to a fourth aspect of the present invention there is provided a method of preparing a composition of the third aspect, the method comprising mixing together one or more compounds of the first aspect with an optional diluent and further optional ingredients The amount of each compound of the first aspect which is used will depend on the exact colour that is desired. It will be appreciated that varying the number of, type and amount of each coloured compound will vary the overall colour of the composition thus obtained.

In preferred embodiments in which the composition of the third aspect is provided as a ready-to-use formulation, the method of the fourth aspect may comprise adding to a diluent one or more compounds of the first aspect.

Alternatively the method of the fourth aspect may comprise adding to a diluent a one or more precursor materials of formula X or X' and one or more thiols of formula XI.

In some preferred embodiments the method of the fourth aspect comprises adding to a diluent a thiol and commercially-available chromophore moiety having appended thereto a vinyl sulfone residue. Examples of such compounds are those sold under the trademark Remazol by Dystar UK and preferred compounds include precursor materials described in relation to the second aspect.

The thiol is preferably a compound of formula $R^2R^3CH_2SH$ wherein $R^2$ and $R^3$ are as defined in relation to the first aspect. Most preferably the thiol is selected from thioglycolic acid, cysteine, cysteamine, N-substituted cysteamines, thioethanol, 1-thiopropane 3-sulfonate and mixtures thereof. Suitable N-substituted cysteamines include compounds of formula $HSCH_2CH_2NR^4R^5$ and $HSCH_2CH_2NHCOR^4$ wherein $R^4$ may be $C_1$ to $C_4$ alkyl and $R^5$ may be hydrogen or $C_1$ to $C_4$ alkyl.

In such embodiments the compounds of the first aspect are formed in situ when the thiol and precursor material are added to the diluent.

Preferably an excess of thiol is added. As described in relation to the third aspect, by excess thiol we mean that a molar excess of total thiol is present when comparing the total amount of thiol to the total amount of precursor materials X or X'. The total thiol includes thiol(s) of formula XI and a second thiol component which may or may not be the same as the thiol(s) of formula XI. In some embodiments the method of the fourth aspect may comprise mixing together approximately equimolar amounts of one or more precursor materials of formula X or X' and one or more thiols of formula XI; allowing these materials to react for a suitable period; and then adding a second thiol component. In preferred embodiments the method of the fourth aspect comprises mixing together one or more precursor materials of formula X or X' with a molar excess of one or more thiols of formula XI.

In embodiments in which the compounds of the first aspect are formed in situ when the thiol and precursor material are added to a diluent, preferably the total amount of thiol (including any second thiol component) added to the diluent is at least 0.01 wt %, preferably at least 0.1 wt %, more preferably at least 0.5 wt %, for example at least 0.8 wt %, preferably at least 1 wt % and most preferably at least 1.2 wt %. In such embodiments, the total amount of thiol added to the diluent may be up to 20 wt %, for example up to 15 wt % or up to 10 wt %. Preferably it is up to 8 wt %, more preferably up to 5 wt %, preferably up to 3 wt %. The above definitions apply to the total amount of all thiol compounds in embodiments in which mixtures are present.

In such embodiments in which a precursor material is added to a diluent, this is added in an amount of at least 0.01 wt %, preferably at least 0.05 wt %, for example at least 0.1 wt % or at least 0.5 wt %. The precursor may be added in an amount of up to 10 wt %, for example up to 5 wt % or up to 3 wt %. The above definitions apply to the total amount of all precursor materials in embodiments in which mixtures are present.

According to a fifth aspect of the present invention there is provided a packaged fibre colouring product comprising a colouring composition comprising compounds of the first aspect or precursors therefor and packaging for said colouring composition.

Any suitable packaging for delivering the reactive dye compounds and compositions of the present invention could be used. Examples of suitable packaging include bottles, pump foamers, and the like. Preferably the packaging is sealed and provides an airtight seal prior to use.

A packaged hair colouring product of the fifth aspect may be a kit comprising a plurality of separate compounds of the first aspect, or precursors thereof. The kit may comprise instructions regarding the co-use of such colouring compositions. They may be used together, for example: by blending them prior to application to hair; or by applying them zonally to hair so as to obtain contrast effects, such as streaks; or by applying them sequentially over the same regions of hair so as to create an appearance of depth or texture in the hair (as opposed to more even appearance which may be produced by one hair colouring composition).

In a packaged fibre (e.g. hair) colouring product of the fifth aspect the product may comprise separate compounds of the first aspect. Alternatively it may comprise precursor compounds which upon admixture prior to application to the fibre substrate form a compound of the first aspect of the present invention. In the case of the kit, it may comprise a plurality of dye-carrying precursors or compositions and a common reactant therefor (for example a compound of formula (XI) as identified above).

Thus, a packaged colouring product of the present invention may comprise a first composition comprising one or more compounds of formula X or X' and a second composition comprising one or more thiols of formula XI. These compositions may suitably be provided in a form such that admixture thereof prior to application to the fibre substrate provides a composition of the third aspect.

In embodiments in which the packaged colouring product comprises two precursor compositions, each composition is individually packaged, preferably in a sealed container. Preferably the second packaged precursor composition comprising one or more thiols of formula XI comprises a molar excess of said compounds compared to the total number of moles of one or more compounds of formula X or X' provided in the first packaged precursor composition.

Suitably simple admixture of the first precursor composition and second precursor composition provides a composition of the third aspect which is ready-to-use. Optional additional ingredients may be included in either the first precursor composition or the second precursor composition or both of these. Such additional ingredients include for example a pH control agent, a thickener and other ingredients, such as described in relation to the third aspect.

In embodiments in which the packaged colouring product comprises a first precursor composition and a second precursor composition, each precursor may comprise part of a bi-component thickening system such that mixing of the two precursor compositions provides a colouring composition of increased viscosity.

Such a thickening system may involve a change of pH on mixing of the two precursor compositions, which will then affect the viscosity of the resultant composition. Bi-component thickening systems may work in different ways but most commonly a change in pH is involved. For example one component may comprise a material, for example as sold by Rohm & Haas under the trade mark Aculyn 22 which is of low viscosity and a free-flowing liquid at low pH (e.g. pH 4) but which increases in viscosity to form a thick paste when the pH is increased (e.g. to pH 8.5).

The properties sought in a thickener system are those which provide the composition with a suitable viscosity profile in order for it to spread across the head easily during the hair dyeing process, and then stay in position on the head when required. The choice of thickening agent or bi-component thickening agent is dependant on the additional components within a composition, and such choices are well known to those skilled in the art. Suitable materials can be found on the INCI list.

Packaged fibre colouring compositions of the present invention may suitably further comprise instructions for application e.g. to hair. They may also include instructions for mixing two or more precursor compositions.

The packaged fibre colouring product of the present invention may comprise a plurality of portions of a composition of the third aspect, or a plurality of portions of precursor compositions. Each such portion may be suitable for a single colouring application.

According to a sixth aspect of the present invention there is provided a method of dyeing fibres (e.g. hair), the method comprising applying to the fibres a composition of the third aspect.

Preferably the method of the sixth aspect is a method of dyeing human hair. Suitably the method comprises applying to the hair the composition at a temperature of between 0° C. and 60° C., for example at a temperature of between 15° C. and 50° C. preferably between 20° C. and 45° C. Suitably the composition applied to the hair has a pH of between 6 and 11, preferably 7 and 10.5, preferably 9 and 10.5. When dyeing human hair at temperatures above ambient temperatures a suitable hood can be employed to achieve the required temperature.

Further preferred features of the composition are as defined in relation to the third aspect. Preferably in the method of the sixth aspect the composition of the third aspect is applied to the hair (preferably the "live"—that is, growing—hair on the head of a human) to provide complete or partial coverage, as desired, and left on the hair for a period of at least 30 seconds, for example at least 1 minute or at least 2 minutes. The composition may be left on the hair for a period of up to 2 hours, for example up to 90 minutes, or up to 60 minutes, up to 45 minutes or up to 30 minutes.

A particular advantage of the present invention is that it allows the colouring of hair to be achieved in a relatively short period, for example from 3 to 20 minutes or 5 to 10 minutes.

Preferably following this period the composition may be rinsed from the hair with water. Suitably it is rinsed with water until the water runs clear and no further colour is rinsed away. In some preferred embodiments the hair is then rinsed with a mildly acidic solution of hydrogen peroxide (preferably of pH 3-6.5, preferably 4.5-5.5), and preferably left for a dwell time of 2-30 minutes, preferably 5-15 minutes; before being again rinsed with water.

Hair treated by the method of the sixth aspect is found to have even colour distribution, and reduced damage to hair is observed.

Further, it has been observed that the colouring compositions of the present invention provide superior wash fastness compared to those of the prior art. For example, following twenty shampooing applications hair coloured by a typical "permanent" colouring composition of the prior art would show some colour fading. However hair coloured by the compositions of the present invention shows substantially no fading after twenty washes.

The method of the sixth aspect of the present invention is preferably a method of colouring human hair, growing on the head. Such a method may include a first step of bleaching the hair prior to adding a composition of the third aspect to provide a lighter initial colour and a different overall result.

This first bleaching step may be carried out by use of percarbamic acid and/or a diacyl percarbamate, generated in situ by the method of the applicant's earlier patent EP 13138308; or by another standard bleaching method of the prior art.

If it is desired to remove the colour from the hair following the colouring method of the sixth aspect of the present invention, this could be achieved by applying to the hair a composition comprising a chemical agent able to reduce the chromophore moiety. Such compositions are well known to those skilled in the art and the removal of the colour in such circumstances is readily achieved.

However, the present inventors have developed a particularly effective composition and method which can be used to remove colour from dyed hair. The method is effective at removing hair dyed using oxidative hair dye compositions of the prior art. However it is particularly effective at removing colour from hair treated according to the method of the sixth aspect. Thus, the present invention may further provide a hair colour removal method.

The colour removal method is not a bleaching method. Indeed the colour removal method of the present invention is particularly advantageous because it does not involve oxidative bleaching of the hair and thus avoids the damage that colour removal by bleaching may cause.

The colour removal method of the present invention can be used to remove colour that has been applied to the hair using the method of the sixth aspect, or it may be used to remove colour from hair which has been dyed using an oxidative dye of the prior art. Such dyes are known to those skilled in the art. Examples of oxidative dyes of the prior art include compounds formed from the reaction of an optionally substituted aniline and an optionally substituted phenol to form an optionally substituted biphenyl compound. Known oxidative dye compositions typically comprise, at a concentration of from 0.01 to 0.05M, for example approximately 0.025M, biphenyl compounds formed by reacting the phenol and aniline components in a 1:1 ratio. Such oxidative dyes of the prior art which can be removed from hair by the colour removal method of the present invention are typically formed by reaction of a phenol and an aniline each of which is substituted with one or more substituents selected from hydroxyl, amino and methyl. Other similar compounds are also used as oxidative dyes and these will be well known to those skilled in the art.

Suitable dyes may be purchased from James Robinson Limited of Huddersfield under the trade mark Jarocol.

The hair colour removal method of the present invention preferably comprises applying to dyed hair, preferably hair dyed by the method of the sixth aspect, a colour removal composition comprising a nucleophile, or a precursor thereof. Preferably the colour removal composition comprises a sulfur-containing nucleophile, or a precursor thereof. Suitable sulfur-containing nucleophiles include thiocyanate, thioglycolic acid, thiocarbamate, carbamoylsulphinic acid and mixtures and/or salts thereof. Alternatively and/or additionally, the colour removal composition may comprise a nucleophile precursor. One suitable nucleophile precursor is thiourea dioxide. Thiourea dioxide is not nucleophilic in itself but rearranges to form formamidine sulfinic acid which hydrolyses to form the nucleophilic species $HSO_2^-$ (hydroxysulfoxylate).

In especially preferred embodiments the sulfur-containing nucleophile comprises a salt of sulphoxylic acid of formula $HSO_2^{-+}M$. M is preferably hydrogen, an alkali metal or a quaternary ammonium species. Such salts may suitably be generated from formamidine sulphinic acid. Under acidic conditions this compound exists as the thiourea dioxide tautomer but under mildly alkaline conditions the formamidine tautomer is formed which hydrolyses to release $HSO_2^{-+}M$ which is believed to be the active dye removal agent. It is also possible to use mixed formamidine/carbamoyl sulphinic acids to generate the reactive species.

The colour removal composition comprises preferably at least 0.1 wt % of the sulfur-containing nucleophile or precursor thereof, for example thiourea dioxide, more preferably at least 1 wt %, most preferably at least 4 wt %.

Suitably the colour removal composition comprises up to 60 wt % of the sulfur-containing nucleophile or precursor thereof, for example thiourea dioxide, preferably up to 45 wt %, more preferably up to 30 wt % and most preferably up to 15 wt %.

In some preferred embodiments when the chromophone moiety D is a premetallised dye comprising a transition metal (for example cobalt or chromium), the colour removal composition further comprises a sequestrant. Any suitable sequestrant known to those skilled in the art may be used. Preferred sequestrants include N-methyl taurine, phosphonates and amine alkyl phosphonates, for example those sold under the trade mark BriQuest and DeQuest, ethylenediaminetetraacetic acid (EDTA) and ethylenediamine disuccinic acid (EDDS).

The colour removal composition may further comprise one or more of a swelling agent, an activator, a diluent, a conditioning agent and a thickener.

The sequestrant, when present, is preferably present in an amount of from 1 to 20 wt %, more preferably 5 to 10 wt %.

Suitable swelling agents include urea.

The colour removal composition preferably comprises at least 0.1 wt % urea, preferably at least 1 wt %, more preferably at least 3 wt %, most preferably at least 5 wt %.

Suitably the colour removal composition comprises up to 60 wt % urea, preferably up to 45 wt %, more preferably up to 30 wt % and most preferably up to 15 wt %.

Suitable activators include divalent and trivalent metal species, for example divalent and/or trivalent ions of zinc, magnesium, aluminium and calcium. Preferably the activator includes zinc or especially magnesium ions. The divalent or trivalent ions may be provided in any suitable form. Preferably they are provided as salts, for example carbonates, sulfates, chlorides, acetates or formates. More preferably they are provided as organic acid salts, for example formate or acetate. Suitably the activator may be selected from zinc acetate, magnesium acetate, zinc oxide, magnesium carbonate, zinc sulphate, aluminium acetate, calcium acetate and mixtures thereof. Zinc acetate and magnesium acetate are particularly preferred.

Acetate or formate salts of divalent or trivalent metals when present may be used directly in the colour removal compositions of the present invention. Alternatively the corresponding acid and a different metal salt may be used, for example magnesium sulphate and acetic acid.

The colour removal composition comprises preferably at least 0.1 wt % of one or more activators, more preferably at least 1 wt %, most preferably at least 4 wt %.

Suitably the colour removal composition comprises up to 60 wt % of one or more activators, preferably up to 45 wt %, more preferably up to 30 wt % and most preferably up to 15 wt %.

The preferred diluent is water. This suitably present in an amount of from 10 to 90 wt %.

Suitable pH buffers include 2-amino-2-methyl-1-propanol.

Suitably the colour removal composition has a pH of from 6 to 12, more preferably from 7.5 to 10.5, and most preferably from 8.5 to 9.5.

A preferred thickener is hydroxyethylcellulose. Preferably the colour removal composition comprises from 1 to 20 wt % of thickeners.

In order to maximise the shelf life of the colour removal composition, it can be packaged as a two component system which could be mixed together shortly before use. By utilising a two pack system, it is possible to make two liquid solutions, that when combined produce a thickened product which is more suitable for use on hair. This can be achieved for example by using a cosmetically approved thickener whose viscosity changes with pH. Suitable ingredients for the colour removal formulations can be found in the INCI list or will be well known to those skilled in the art. Such systems are described above in relation to the packaged hair colouring compositions of the fifth aspect of the present invention.

In the colour removal method of the present invention, the colour removal composition is suitably applied to the hair and maintained on the head at a temperature of from 10 to 75° C., preferably from 20 to 70° C., more preferably from 30 to 65° C.

When removing colour from human hair at temperatures above ambient temperature a suitable hood can be employed to achieve the required temperature.

Suitably complete colour removal is effected after a period of 5 to 60, for example 15 to 30 minutes.

Suitably the colour removal composition is left in the hair for a period of from 0.1 to 60 minutes, preferably 0.5 to 30 minutes for example 1 to 15 minutes.

The colour removal method of the present invention has been found to be very effective. Hair has been found to return to its original colour prior to being dyed without any visible damage occurring. In embodiments in which an initial bleaching step has been carried out, hair has been found to return to its bleached colour.

This method offers considerable advantages over colour removal methods of the prior art which rely on bleaching the hair. Such bleaching colour removal methods of the prior art cause considerable damage to hair (particularly in the case of hair which is repeatedly dyed and oxidatively bleached) and often do not provide the original colour.

The present invention thus provides a hair treatment method comprising the steps of:

(a) optionally bleaching the hair;

(b) dyeing the hair by applying a composition of the third aspect; and (c) optionally removing colour from the hair by applying a colour removal composition comprising a sulfur-containing nucleophile.

Preferred aspects of each of steps (a), (b) and (c) are described above. Steps (b) and (c) may be repeated without any significant damage occurring to hair. Preferably steps (b) and (c) may be each repeated two or more, preferably five or more, for example ten or more times without any significant increased damage to the hair being observed.

Step (a) is an optional initial bleaching step, which may be carried out using any suitable bleaching method of the prior art. This is carried out if it is desired to lighten the initial colour of hair prior to a first dyeing step. However, once a first colour has been applied, there is no need to again bleach the hair further to remove this colour as this can be carried out in step (c). Step (a) would be repeated only if a lighter base shade is required. Of course it will also be necessary to bleach new hair which has grown since previous colouring.

Because steps (b) and (c) can be carried out rapidly, it would be possible for a user to dye a small portion of hair (either on or off the head) to see exactly the colour that would be achieved and remove this colour if it was not desirable.

The colouring method of the present invention is highly reproducible, rapidly develops to full colour, is resistant to fade and readily removable, and thus offers considerable advantages over the prior art.

According to a seventh aspect of the present invention there is provided the use of compounds of the first aspect to colour human hair. The use of the compounds of the present invention provides numerous advantages over colouring compounds of the prior art, such as are described herein.

The present invention is represented by the following non-limiting examples.

Percentage values herein denote the weight of a given component expressed as a percentage of the total weight of the composition in which it is present unless otherwise stated.

In these examples, suitable conditions are given for hair dyeing and colour removal. However it will be appreciated that these conditions could be modified as appropriate depending on the hair being treated and the equipment available in the salon.

EXAMPLES

Example 1

Synthesis of Carboxymethylthiolethylsulphone Dye Using Remazol Dyes as Starting Materials A carboxymethylthiolethylsulphone dye may be prepared using the synthesis route as illustrated in Diagram 1.

FIG. 1

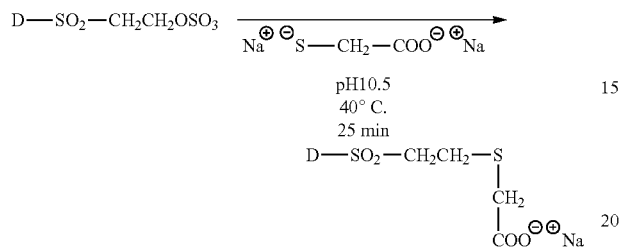

In the reaction scheme D is a chromophore and varies depending on which starting dye is used. In the present example a variety of Remazol® dyes commercially available from Dystar are used as starting materials, in particular, Remazol Black B, Remazol Yellow GS, Remazol Orange G, Remazol Red B, Remazol Blue R, Remazol Blue B, and others mentioned in examples herein.

Synthesis of Carboxymethylthiolethylsulphone Dye

An aqueous dye solution (0.1 mol/100 ml, pH 10.5) of a purified Remazol® dye is prepared. To this solution, a 0.1 mol solution of sodium thioglycollate (pH10.5) is added by slow dripping at a temperature of between 23 and 25° C.

After the addition of sodium thioglycollate, the pH of the system is maintained at pH10.5 using sodium carbonate. The reaction is then allowed to proceed, at 20-25° C. and pH10.5, for 5-8 hours. At the end of the synthesis, the pH of the system is reduced to below pH 2, which precipitates the carboxymethylthiolethylsulphone dye compounds which are then isolated by filtration and washing.

Example 2

Synthesis of Hydroxyethylthioethylsulphone Dye

The hydroxyethylthioethylsulphone dye may be prepared using the synthesis route as illustrated in FIG. 2.

FIG. 2

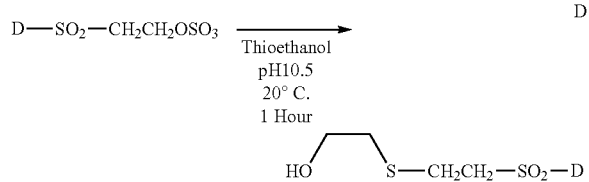

In the reaction scheme D is a chromophore and varies depending on which starting dye is used. In the present example Remazol Orange G is used as the starting material, but other suitable sulphatoethylsulphone dye compounds can also be used as starting materials such as Remazol Yellow and Remazol Brilliant Blue R.

0.1 mole of Remazol Orange G dye is dissolved in 150 ml of distilled water adjusted to pH10.5 using sodium carbonate, and added to a flask. The flask is placed in a water bath. 0.1 moles of thioethanol is then added drop-wise, to the reaction mixture under stirring. The total addition time is one hour. The pH of the reaction scheme is maintained at pH10.5 and the temperature of the reaction system 20-25° C. during addition of thioethanol. The reaction is then allowed to proceed at 20-25° C. and pH10.5 (which is corrected as necessary using sodium carbonate) for 5 hours. The endpoint of the reaction is indicated by the pH remaining constant for more than 5 minutes. At this point, the hydroxyethylthioethylsulphone dye is obtained. The pH of the system is then reduced to pH2 and KCl (35% of the total solution) is then added to the reaction mixture in order to precipitate the dye. Filtration using Whatman filter paper follows. The precipitate is then washed with acetone for 4-5 times (50 ml of acetone used each time) to obtain the final dye product.

Example 3

Synthesis of Monothiosuccinate-S-Ethylsulphone Dye

The monothiosuccinate-S-ethylsulphone dye may be prepared using the synthesis route as illustrated in FIG. 3.

FIG. 3

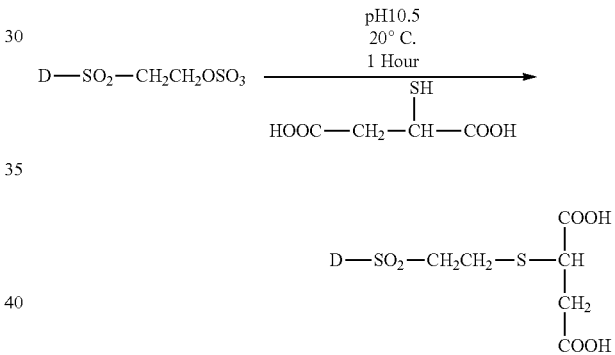

In the reaction scheme, D is a chromophore and varies depending on which starting dye is used. In the present example Remazol Orange G is used as the starting material, but other suitable sulphatoethylsulphone dye compounds can also be used as starting materials, such as Remazol Yellow and Remazol Brilliant Blue R.

0.1 moles of pure Remazol Orange G dye and 150 ml of distilled water are introduced into a 400 ml flask and the pH adjusted to pH10.5 using sodium carbonate. The flask is placed in a water bath. 0.1 moles of thiosuccinic acid is then added dropwise with stirring. The addition time is 1-1.5 hours. The pH of the reaction system is maintained at pH10.5 and the temperature of the reaction system is 20-25° C. throughout the addition of thiosuccinic acid.

The reaction is then allowed to proceed, at 20-25° C. and pH10.5 (which is adjusted as necessary using sodium carbonate) for 6 hours. Using 6N HCl, the pH of the system is then reduced to pH2. KCl (35% of the total solution) is then added to the reaction mixture in order to precipitate the dye. Filtration using Whatman paper follows. The precipitate is then washed with acetone for 4-5 times (50 ml of acetone is used each time) to obtain the final dye product.

Example 4

An acrylamido dye precursor of general formula

Ar—N=N—[H-acid]-NH—(C=O)—CH=CH$_2$—
illustrative of class (X) defined above—was prepared as follows:

Aniline (0.1 mole) was dissolved in 0.1 molar HCL (50 ml), cooled in an ice-bath to 0-5 C and then reacted with nitrous acid (1.2 moles of NaNO$_2$ dissolve in minimum 0.1 M HCl dripped in slowly over 30 mins.)—diazotisation was complete at this stage. Excess nitrous acid was removed by adding 0.5 moles of urea.

The above diazonium salt was then added slowly, at 0-5° C., to an aqueous alkaline solution of H-acid (1 mole of naphthalene-1-amino-2-hydroxy-3,6-disulphonic acid) buffered at pH 10 with excess sodium carbonate; instantly a bright bluish red colour was formed in solution. The reaction was stirred for a further 60 minutes. Still maintaining the pH at 10 and the temperature at 0-5° C., acryloyl chloride was solely dripped into the stirred mixture. Reaction continued a further 1 h under these conditions—at this stage the system was tested for free aromatic amine (Ehrlich test) and if none was detected the product isolate by the addition of sufficient saturated salt solution. Filtration and washing with saturated salt solution and ethanol, then drying completed the process. The isolated acrylamido dye was found to have a purity greater than 95% (HPLC).

The brilliant, bluish-red dye precursor, of formula X, has the following structure:

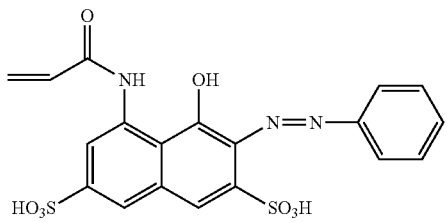

This dye precursor may be onward reacted as described above to make a dye compound of formula (I) of the invention.

Example 5

Dye solutions can be made up using compounds prepared according to Example 1 and packaged in a suitable bottle-type package.

5a-Auburn Dye

| Ingredients | % |
| --- | --- |
| Urea | 10.00 |
| Cocamidopropyl Betaine | 0.80 |
| Dye prepared according to Example 1 using Remazol Orange G | 0.23 |
| Dye prepared according to Example 1 using Remazol Yellow GS | 0.42 |
| Dye prepared according to Example 1 using Remazol Black B | 0.35 |
| Thioglycolic Acid 80% | 2.5 |
| Triethanolamine 99% | 50.74 |
| Ammonium Hydroxide 29% | 9.00 |
| Water | To 100 |

5b-Light Brown Dye

| Ingredients | % |
| --- | --- |
| Urea | 10.00 |
| Cocamidopropyl Betaine | 0.80 |
| Dye prepared according to Example 1 using Remazol Red B | 0.010 |
| Dye prepared according to Example 1 using Remazol Yellow GS | 0.226 |
| Dye prepared according to Example 1 using Remazol Blue B | 0.678 |
| Thioglycolic Acid 80% | 2.5 |
| Triethanolamine 99% | 50.74 |
| Ammonium Hydroxide 29% | 9.00 |
| Water | To 100 |

5c-Champagne Blonde Dye

| Ingredients | % |
| --- | --- |
| Urea | 10.00 |
| Cocamidopropyl Betaine | 0.80 |
| Dye prepared according to Example 1 using Remazol Red 5B | 0.023 |
| Dye prepared according to Example 1 using Remazol Golden Yellow GR | 0.465 |
| Dye prepared according to Example 1 using Remazol Blue BS | 0.512 |
| Thioglycolic Acid 80% | 2.5 |
| Triethanolamine 99% | 50.74 |
| Ammonium Hydroxide 29% | 9.00 |
| Water | To 100 |

5d-Auburn Dye

| Ingredients | % |
| --- | --- |
| Urea | 10.00 |
| Cocamidopropyl Betaine | 0.80 |
| Dye prepared according to Example 1 using Remazol Red B | 0.023 |
| Dye prepared according to Example 1 using Remazol Golden Yellow GS | 0.42 |
| Dye prepared according to Example 1 using Remazol Blue B | 0.35 |
| Thioglycolic Acid 80% | 2.5 |
| Ammonium Hydroxide 29% | 11.48 |
| Water | To 100 |

5e-Light Brown Dye

| Ingredients | % |
| --- | --- |
| Urea | 10.00 |
| Cocamidopropyl Betaine | 0.80 |
| Dye prepared according to Example 1 using Remazol Red RS | 0.010 |
| Dye prepared according to Example 1 using Remazol Yellow G | 0.226 |
| Dye prepared according to Example 1 using Remazol Blue B | 0.678 |

5e-Light Brown Dye

| Ingredients | % |
| --- | --- |
| Thioglycolic Acid 80% | 2.5 |
| Ammonium Hydroxide 29% | 11.48 |
| Water | To 100 |

Example 6

Dye solutions can be made up using compounds prepared according to Example 1 and packaged in a suitable bottle-type package.

6a - Plum Silver

| Ingredients | % |
| --- | --- |
| Urea | 10.0000 |
| Cocamidopropyl Betaine | 0.8000 |
| Dye prepared according to Example 1 using Remazol Golden Yellow RNL 150% | 0.0632 |
| Dye prepared according to Example 1 using Remazol Brilliant Red F3B gran | 0.0628 |
| Dye prepared according to Example 1 using Remazol Black B | 0.0408 |
| Thioglycolic Acid 80% | 6.0000 |
| Ammonium Hydroxide 29% | 6.2000 |
| Water | To 100% |

6b - Golden Brown

| Ingredients | % |
| --- | --- |
| Urea | 10.0000 |
| Cocamidopropyl Betaine | 0.8000 |
| Dye prepared according to Example 1 using Remazol Golden Yellow RNL 150% | 1.3924 |
| Dye prepared according to Example 1 using Remazol Orange | 1.0000 |
| Dye prepared according to Example 1 using Remazol Black GWF | 0.7116 |
| Thioglycolic Acid 80% | 6.0000 |
| Ammonium Hydroxide 29% | 6.2000 |
| Water | To 100% |

6c - Aubergine

| Ingredients | % |
| --- | --- |
| Urea | 10.0000 |
| Cocamidopropyl Betaine | 0.8000 |
| Dye prepared according to Example 1 using Remazol Golden Yellow RNL 150% | 0.1024 |
| Dye prepared according to Example 1 using Remazol Brilliant Red F3B gran | 1.0072 |
| Dye prepared according to Example 1 using Remazol Black B | 0.9920 |
| Thioglycolic Acid 80% | 6.0000 |
| Ammonium Hydroxide 29% | 6.2000 |
| Water | To 100% |

6d - Candy Floss

| Ingredients | % |
| --- | --- |
| Urea | 10.0000 |
| Cocamidopropyl Betaine | 0.8000 |
| Dye prepared according to Example 1 using Remazol Brilliant Red F3B gran | 0.1036 |
| Thioglycolic Acid 80% | 6.0000 |
| Ammonium Hydroxide 29% | 6.2000 |
| Water | To 100% |

6e - Chestnut Brown

| Ingredients | % |
| --- | --- |
| Urea | 10.0000 |
| Cocamidopropyl Betaine | 0.8000 |
| Dye prepared according to Example 1 using Remazol Golden Yellow RNL 150% | 1.5368 |
| Dye prepared according to Example 1 using Remazol Brilliant Red F3B gran | 0.9924 |
| Dye prepared according to Example 1 using Remazol Black GWF | 0.9872 |
| Thioglycolic Acid 80% | 6.0000 |
| Ammonium Hydroxide 29% | 6.2000 |
| Water | To 100% |

6f - Mid Brown

| Ingredients | % |
| --- | --- |
| Urea | 10.0000 |
| Cocamidopropyl Betaine | 0.8000 |
| Dye prepared according to Example 1 using Remazor Golden Yellow RNL 150% | 0.8088 |
| Dye prepared according to Example 1 using Remazor Brilliant Red F3B gran | 0.4136 |
| Dye prepared according to Example 1 using Remazor Black GWF | 0.3948 |
| Thioglycolic Acid 80% | 6.0000 |
| Ammonium Hydroxide 29% | 6.2000 |
| Water | To 100% |

6g - Burgundy Desire

| Ingredients | % |
| --- | --- |
| Urea | 10.0000 |
| Cocamidopropyl Betaine | 0.8000 |
| Dye prepared according to Example 1 using Remazol Golden Yellow RNL 150% | 1.4908 |
| Dye prepared according to Example 1 using Remazol Brilliant Red F3B gran | 1.5164 |
| Dye prepared according to Example 1 using Remazol Black GWF | 0.2988 |
| Thioglycolic Acid 80% | 6.0000 |
| Ammonium Hydroxide 29% | 6.2000 |
| Water | To 100% |

6h - Tangerine Spark

| Ingredients | % |
|---|---|
| Urea | 10.0000 |
| Cocamidopropyl Betaine | 0.8000 |
| Dye prepared according to Example 1 using Remazol Golden Yellow RNL 150% | 0.5344 |
| Dye prepared according to Example 1 using Remazol Brilliant Red F3B gran | 0.1900 |
| Dye prepared according to Example 1 using Remazol Orange 3R Spec gran | 1.0476 |
| Thioglycolic Acid 80% | 6.0000 |
| Ammonium Hydroxide 29% | 6.2000 |
| Water | To 100% |

6i - Midnight Black

| Ingredients | % |
|---|---|
| Urea | 10.0000 |
| Cocamidopropyl Betaine | 0.8000 |
| Dye prepared according to Example 1 using Remazol Orange 3R Spec gran | 1.0264 |
| Dye prepared according to Example 1 using Remazol Black B | 3.9836 |
| Thioglycolic Acid 80% | 6.0000 |
| Ammonium Hydroxide 29% | 6.2000 |
| Water | To 100% |

6j - Chocolate Brown

| Ingredients | % |
|---|---|
| Urea | 10.0000 |
| Cocamidopropyl Betaine | 0.8000 |
| Dye prepared according to Example 1 using Remazol Golden Yellow RNL 150% | 0.5700 |
| Dye prepared according to Example 1 using Remazol Orange 3R Spec gran | 0.9844 |
| Dye prepared according to Example 1 using Remazol Black GWF | 0.9740 |
| Thioglycolic Acid 80% | 6.0000 |
| Ammonium Hydroxide 29% | 6.2000 |
| Water | To 100% |

6k - Harvest Blonde

| Ingredients | % |
|---|---|
| Urea | 10.0000 |
| Cocamidopropyl Betaine | 0.8000 |
| Dye prepared according to Example 1 using Remazol Golden Yellow RNL 150% | 0.0992 |
| Dye prepared according to Example 1 using Remazol Brilliant Yellow 4GL | 0.0992 |
| Dye prepared according to Example 1 using Remazol Orange 3R Spec gran | 0.0780 |
| Thioglycolic Acid 80% | 6.0000 |
| Ammonium Hydroxide 29% | 6.2000 |
| Water | To 100% |

6l - Strawberry Blonde

| Ingredients | % |
|---|---|
| Urea | 10.0000 |
| Cocamidopropyl Betaine | 0.8000 |
| Dye prepared according to Example 1 using Remazol Brilliant Red F3B gran | 0.0208 |
| Dye prepared according to Example 1 using Remazol Golden Yellow RNL 150% | 0.0622 |
| Thioglycolic Acid 80% | 6.0000 |
| Ammonium Hydroxide 29% | 6.2000 |
| Water | To 100% |

Percentage values herein, including in relation to Examples 5 and 6, denote the weight of a given component expressed as a percentage of the total weight of the composition in which it is present.

Any of the compounds prepared according to Examples 1 to 4 can be substituted for the compounds in the dye compositions of Examples 5 and 6 above. In particular, the packaged hair colouring compositions of the examples provide improvements in terms of consumer acceptance since no admixing of ingredients is necessary before dyeing, and improved wash fastness.

The compositions of Examples 5 and 6 are merely illustrative of the shades which can be produced, in accordance with the present invention. Essentially there is no limit to the shades which can be produced.

The compositions of Example 6 have a higher thioglycolic acid content than the compositions of Example 5 and may be especially suitable in order to achieve a high level of reacted-on dye on the hair, in order to achieve a strong coloration effect and/or to obtain rapid coloration. Rapid reaction to the hair, and hence rapid coloration, is believed to be promoted by a higher level of thioglycolic acid.

An aim of the invention is to achieve the desired coloration with quantitative reaction of the dye molecules applied (i.e. exhaustion of dye molecules); thus with no wash-off of dye molecules. Of course this is an idealised aim and take-up may be affected by many things, but the amount of thioglycolic acid is believed to be an important factor.

Example 7

The compositions of Examples 5 and 6 may typically be applied using the following regime:

Rub colouration mixture into hair and leave at 25° C. for 10 minutes using a liquor ratio of 2.5:1 (2.5 g of preparation mixture: 1 g hair tress)

Rinse with cold or warm water

After-treatment: 10 minutes at 25° C. using 2.5 g (same liquor ratio as above) of a 30 g/l Hydrogen Peroxide soln (36%), pH of approximately 5.

Rinse with water

Shampoo

Rinse with water

Dry

Example 8a

A sample of hair having an initial bleached blonde appearance was treated as follows.

| Part 1 | | Part 2 | |
|---|---|---|---|
| 37.04% | Urea | 88.16% | Water |
| 3.70% | Laurylamidopropylbetaine | 2.52% | Thioglycollic acid |
| 37.04% | Water | 2.52% | Sodium sulphite |
| 18.52% | 1 part Remazol Brilliant Red F3B<br>1 part Remazol Golden Yellow RNL<br>1 part Remazol Brilliant Orange 3R | 4.28% | 2-amino-2-methyl-1-propanol |
| 3.70% | Hydroxyethylcellulose | 2.52% | Hydroxyethylcellulose |

Percentage values in the table above denote the weight of a given component expressed as a percentage of the total weight of the composition of the part in which it is present.

Prepare hair treatment mixture, by mixing 3.2 g of part 1 and 7.9 g of Part 2.
Brush mixture into hair and leave at 40° C. for 15 minutes using a liquor ratio of 2.5:1 (2.5 g of preparation mixture: 1 g hair tress).
Rinse with warm water.
Massage an after-treatment solution of 30 g/l hydrogen peroxide soln (36%) using same liquor ratio as above.
Rinse with water
Shampoo
Rinse with water
Dry as required The resulting hair was a bright red colour that was found to exhibit no visible fade or colour change after 20 shampoo washes.

Example 8b

A sample of hair having an initial bleached blonde appearance was treated as follows.

| Part 1 | | Part 2 | |
|---|---|---|---|
| 37.04% | Urea | 88.16% | Water |
| 3.70% | Laurylamido-propylbetaine | 2.52% | Thioglycollic acid |
| 37.04% | Water | 2.52% | Sodium sulphite |
| 18.52% | 1 part Remazol Brilliant Red F3B<br>1 part Remazol Brilliant Yellow 4GL<br>1 part Remazol Brilliant Orange 3R | 4.28% | 2-amino-2-methyl-1-propanol |
| 3.70% | Hydroxyethylcellulose | 2.52% | Hydroxyethylcellulose |

Percentage values in the table above denote the weight of a given component expressed as a percentage of the total weight of the composition of the part in which it is present.

Prepare hair treatment mixture, by mixing 3.2 g of part 1 and 7.9 g of Part 2.
Brush mixture into hair and leave at 40° C. for 15 minutes using a liquor ratio of 2.5:1 (2.5 g of preparation mixture: 1 g hair tress).
Rinse with warm water.
Massage an after-treatment solution of 30 g/l hydrogen peroxide soln (36%) using same liquor ratio as above.
Rinse with water
Shampoo
Rinse with water
Dry as required The resulting hair was a bright orange colour that was found to exhibit no visible fade or colour change after 20 shampoo washes.

Example 8c

A sample of hair produced from example 8b having an initial bright orange appearance was treated as follows.

| Part 1 | | Part 2 | |
|---|---|---|---|
| 50% | Urea | 92.86% | Water |
| 25% | Thiourea dioxide | 5.84% | 2-amino-2-methyl-1-propanol |
| 25% | Zinc acetate | 1.08% | Laurylamidopropylbetaine |
| | | 0.22% | Hydroxyethylcellulose |

Percentage values in the table above denote the weight of a given component expressed as a percentage of the total weight of the composition of the part in which it is present.

Prepare hair treatment mixture, by mixing 2.0 g of part 1 and 9.3 g of Part 2.
Brush mixture into hair and leave at 30° C. for 25 minutes using a liquor ratio of 2.5:1 (2.5 g of preparation mixture: 1 g hair tress).
Rinse with warm water.
Dry as required The resulting hair was a blonde colour with no hint of the previous colour and with little or no damage.

Example 8d

A process where hair treated in example 8c is then coloured using the method in example 8b to give bright orange coloured hair which was found to exhibit no visible fade or colour change after 20 shampoo washes.

Example 8e

A process where hair treated in example 8d is then treated with the colour removal system as described in example 8c to give a blonde coloured hair with little or no damage.

Example 8f

The process of example 8c was repeated except that the colour removal composition was left on the hair for 15 minutes at a temperature of 60° C. Again, the resulting hair was a blonde colour with no hint of the previous colour and with little or no damage.

What is claimed is:

1. A method of removing colour from dyed hair, the method comprising applying to the hair a colour removal composition comprising a sulfur-containing nucleophile or a precursor thereof selected from a group consisting of: thiocyanate, thioglycolic acid, thiocarbamate, carbamoylsulphinic acid, formamidine sulfinic acid, and mixtures and/or salts thereof.

2. The method of claim 1, wherein the sulfur-containing nucleophile precursor is thiourea dioxide.

3. The method of claim 1,
wherein the dyed hair was dyed with a dying composition including:
a compound of formula (I)

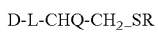  (I)

wherein:
D is a chromophore;
L is a linking group selected from $SO_2$, NHCO, and $NHSO_2$;
Q is a hydrogen or halogen atom; and
R is selected from $C_1$-$C_4$ alkyl, $(CHA_nCOOH, (CH_2)_nCONH_2, (CH_2)_nSO_3H, (CH_2)_nCOOM, (CH_2)_nPO_3H, (CH_2)_nOH, (CH_2)_nSSO_3^-, (CH_2)_nNR^1_2, (CH_2)_nN^+R^1H_2, (CH_2)_nNHCOR^1, PhSSO_3^-, PhSO_3H, PhPO_3H, PhNR^1_2, PhN^+R^1_3, (CH_2)_2CH(SH)R^1 (CH_2)_3COOH$,

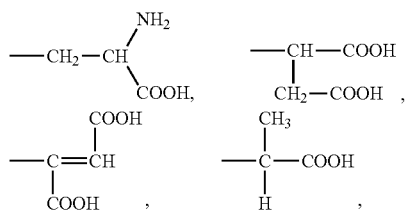

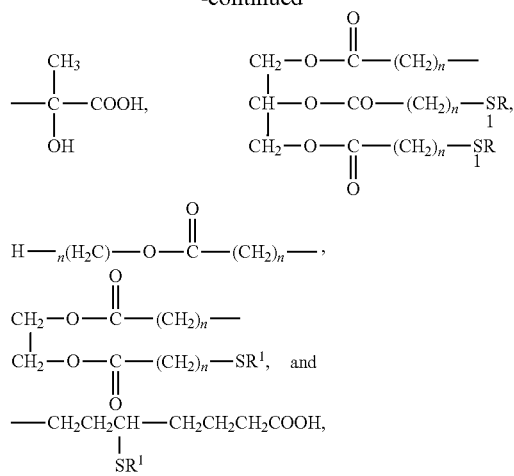

wherein n is an integer in the range of 1 to 4 wherein within the same molecule each n is not necessarily the same integer; M is a cation of an alkaline earth metal, alkali metal, $NH_4^+$ or $NR^1_3{}^+$; and $R^1$ is $C_1$-$C_4$ alkyl; and
at least one of the following: a diluent or a carrier.

4. The method of claim 3, wherein the dying composition further includes a thiol selected from a group consisting of: thioglycolic acid, thiolactic acid, dihydrolipoate, thioglycerol, mercaptopropionic acid, cysteine, N-substituted cysteines, cysteamines, N-substituted cysteamines, thioethanol and 1-thiopropane 3-sulfonate.

5. The method of claim 3, wherein the dying composition further includes urea.

* * * * *